United States Patent [19]

Vicenzi et al.

[11] Patent Number: 5,977,383

[45] Date of Patent: Nov. 2, 1999

[54] PROCESS FOR THE SYNTHESIS OF BENZOTHIOPHENES

[75] Inventors: Jeffrey Thomas Vicenzi, Brownsburg; Tony Yantao Zhang, Indianapolis, both of Ind.

[73] Assignee: Eli Lilly and Company, Indianapolis, Ind.

[21] Appl. No.: 08/934,999

[22] Filed: Sep. 22, 1997

Related U.S. Application Data

[60] Provisional application No. 60/026,695, Sep. 25, 1996.

[51] Int. Cl.$^6$ ................................................. C07D 333/56
[52] U.S. Cl. ............................................................ 549/58
[58] Field of Search .................................................. 549/58

[56] References Cited

U.S. PATENT DOCUMENTS

| | | | |
|---|---|---|---|
| 3,394,125 | 7/1968 | Crenshaw | 548/525 |
| 3,413,305 | 11/1968 | Crenshaw | 548/525 |
| 4,133,814 | 1/1979 | Jones et al. | 260/326 |
| 4,230,862 | 10/1980 | Suarez et al. | 546/237 |
| 4,233,333 | 11/1980 | Trummlitz et al. | 549/62 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 4,436,748 | 3/1984 | Ong et al. | 549/51 |
| 4,544,746 | 10/1985 | Holtje | 546/103 |
| 5,292,894 | 3/1994 | Ebel et al. | 549/52 |
| 5,395,842 | 3/1995 | Labrie | 514/320 |
| 5,470,854 | 11/1995 | Angerer et al. | 514/233 |
| 5,472,962 | 12/1995 | Kiozumi et al. | 514/233.5 |

FOREIGN PATENT DOCUMENTS

| | | |
|---|---|---|
| 0062504 A1 | 10/1982 | European Pat. Off. . |
| 062 503 | 10/1982 | European Pat. Off. . |
| 0556680 A1 | 2/1993 | European Pat. Off. . |
| WO 89/0289 | 4/1989 | WIPO . |
| WO 95/10513 | 4/1995 | WIPO . |

OTHER PUBLICATIONS

Crenshaw, R.R., et al, *J. Med. Chem.* 14(12):1185–1190 (1971).

Jones, C.D., et al, *J. Med. Chem.* 27: 1057–1066) 1984.

Jones, C.D., et al, *J. Med. Chem.* 35: 931–938 1992.

Guy, "Utilization of Polyphosphonic Acid in the Presence of a Co–solvent," *Synthesis,* 222–223, (Mar., 1985).

Ple, et al., "Synthesis of Substituted Benzo [b] by Thiophene, [b] Acid–Catalyzed Cyclization of Thiophenyl Acctals and Ketone", *J. Heterocyclic Chem.,* 25, 1271–1272 (1988).

Kost et al., "Isomerization of 3–Substitutal Indoles, Benzo Furens, and Benzo[b] Thiophenes", Translated from *Zhurnal Organicheskoi Khimii,* vol. 6, No. 7, pp. 1503–1505 (Jul. 1970).

Merck Index, 1983, 10$^{th}$ Ed. Entry 7453.

Chemical Abstract vol. 90 No. 103 801, Corn et al, "Tetrlhydrofurate" 1978.

*Primary Examiner*—John Kight
*Assistant Examiner*—Raymond Covington
*Attorney, Agent, or Firm*—Gilbert T. Voy

[57] ABSTRACT

The instant invention provides improved processes for preparing benzothiophenes utilizing cation exchange resins.

12 Claims, No Drawings

PROCESS FOR THE SYNTHESIS OF BENZOTHIOPHENES

This application claims the benefit of U.S. Provisional Application No. 60/026,695 filed on Sep. 5, 1996.

BACKGROUND OF THE INVENTION

This invention relates to the field of pharmaceutical chemistry, and provides an advantageous process for preparing a group of benzothiophenes from dialkoxyacetophenones. The process provides the desired compounds in excellent yield on a large scale.

The preparation of benzothiophenes through a dialkoxy benzothiophene intermediate was previously described in U.S. Pat. No. 4,380,635, the disclosure of which is herein incorporated by reference, which teaches the intramolecular cyclization of α-(3-methoxyphenylthio)-4-methoxyacetophenone in the presence polyphosphoric acid (PPA). Heating the acetophenone starting material in PPA at about 85° C. for about 1 hour provides an approximately 3:1 mixture of two isomers, 6-methoxy-2-(4-methoxyphenyl)benzo[b]thiophene and 4-methoxy-2-(4-methoxyphenyl)benzo[b]thiophene. However, when this reaction is conducted on a manufacturing scale, the isomeric benzothiophenes precipitate and produce a thick paste that cannot be stirred adequately in conventional manufacturing equipment.

Use of a solvent to alleviate the problem caused by a paste in a different reaction scheme has been attempted by Guy et al., *Synthesis*, 222 (1980). However, when this approach is applied to the instant scheme, the addition of a solvent results in incomplete cyclization of the starting acetophenone, incomplete rearrangement of 6-methoxy-3-(4-methoxyphenyl)benzo[b]thiophene, and dramatically increased reaction times.

Thus, there is a need for an improved process which employs alternate catalysts for the conversion of dialkoxyacetophenone derivatives to benzothiophenes with suitable yields and acceptable reaction times.

SUMMARY OF THE INVENTION

The present invention provides a process for the preparation of benzothiophenes utilizing a cation exchange resin. This preparation relies on an intramolecular cyclization of a dialkoxyacetophenone derivative to yield a benzothiophene.

Thus, the invention provides a process for preparing a compound of formula I

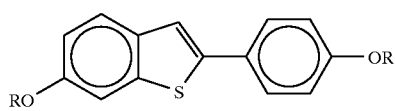

I wherein the R groups are the same or different, and represent $C_1$–$C_6$ alkyl; which includes cyclizing a compound of formula II

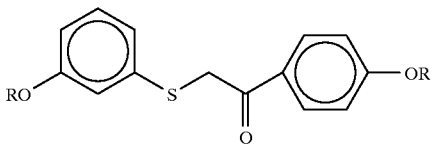

II wherein the R groups are defined as above, in the presence of a cation exchange resin.

DETAILED DESCRIPTION OF THE INVENTION

Benzothiophene is a key intermediate in the synthesis of raloxifene, a selective estrogen receptor modulator, or SERM. In addition to providing an improved process for the preparation of this intermediate, the present invention additionally provides an improved process for preparing a compound of formula III

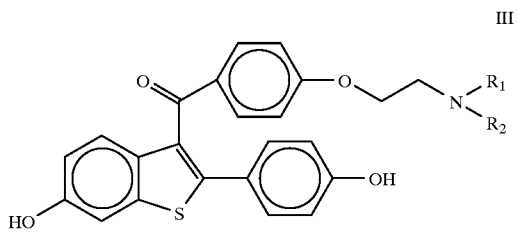

III wherein:

$R_1$ and $R_2$ are independently $C_1$–$C_6$ alkyl, or combine to form, with the nitrogen to which they are attached, piperidinyl, pyrrolidinyl, methylpyrrolidinyl, dimethylpyrrolidinyl, or hexamethyleneimino, or the pharmaceutically acceptable salts or solvates thereof; which includes cyclizing a compound of formula II

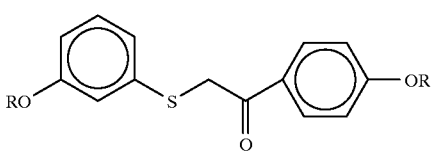

II wherein the R groups are the same or different, and represent $C_1$–$C_6$ alkyl, in the presence of a cation exchange resin.

Many of the starting materials and compounds prepared by the process of this invention are further provided in U.S. Pat. No. 4,133,814 and U.S. Pat. No. 4,380,635, the disclosures of which are herein incorporated by reference.

In this document, all temperatures will be stated in degrees Celsius. All amounts, ratios, concentrations, proportions and the like will be stated in weight units, unless otherwise stated, except for ratios of solvents, which are in volume units.

The term "acid catalyst" used herein represents a Lewis acid or a Brønsted acid. Representative Lewis acids are zinc chloride, zinc iodide, aluminum chloride, and aluminum bromide. Representative Bronsted acids include inorganic acids, such as sulfuric and phosphoric acids, carboxylic acids, such as acetic and trifluorocetic acids, sulfonic acids, such as methanesulfonic, benzenesulfonic, 1-naphthalenesulfonic, 1-butanesulfonic, ethanesulfonic, 4-ethylbenzenesulfonic, 1-hexanesulfonic, 1,5-naphthalenedisulfonic, 1-octanesulfonic, camphorsulfonic, trifluoromethanesulfonic, and p-toluene-sulfonic acids. Additionally, the term "acid catalyst" includes cation exchange resins, which may also be referred to as resin-based acid catalysts. These cation exchange resins are by definition insoluble, acidic resins. Said cation exchange resins includes, but is not limited to cation exchangers on dextran, such as, for example, CM Sephadex (carboxymethyl Sephadex), SP Sephadex (Sulfopropyl Sephadex), and the like; cation exchangers on agarose, such as, for example, CM Sepharose, S Sepharose, and the like; cation exchangers on cellulose, such as, for example, CM Cellulose, Cellulose Phosphate, Sulfoxyethyl Cellulose, and the like; cation exchangers on polystyrene, such as, for example, sulfonated polystyrene resins (which typically differ in the overall number of sulfonic acid groups on the resin), including Amberlyst® XN-1010, Amberlyst® 15, Amberlite®, XE586®, and the like; sulfonated polyfluorocarbon resins, including Nafion-H® resin; Oxycellulose; SP Trisacryl® resins, such as, for example, SP Trisacryl Plus M® and SP Trisacryl Plus LS®; poly (N-tris [hydroxymethyl]methyl methacrylamide resin; and the like.

The term "halo" refers to fluoro, chloro, bromo, or iodo groups.

The term "$C_1$–$C_6$ alkyl" represents a straight or branched alkyl chain having from one to six carbon atoms. Typical $C_1$–$C_6$ alkyl groups include methyl, ethyl, n-propyl, isopropyl, n-butyl, isobutyl, sec-butyl, t-butyl, n-pentyl, isopentyl, n-hexyl, 2-methylpentyl, and the like. The term "$C_1$–$C_4$ alkyl" represents a straight or branched alkyl chain having from one to four carbon atoms, and includes methyl, ethyl, n-propyl, isopropyl, n-butyl, sec-butyl, i-butyl, and t-butyl.

Appropriate activating ester groups are known in the art. Numerous reactions for the formation and removal of protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for nonregioselective removal of hydroxy protecting groups, particularly methyl, are known in the art. Compounds of formula III which have previously been protected at the 6- and 4'-position with methoxy may be selectively cleaved to generate compounds of formula III with a 4'-methoxy group. In general, the procedure for cleavage of a methoxy group on the 4' position involves the combination of a 6-, 4'- dimethoxy substrate with a demethylation reagent chosen from the group of boron tribromide, boron trichloride, or boron triiodide, or with AlCl3 and various thiol reagents, such as EtSH. The reaction is conducted under an inert atmosphere such as nitrogen, with one or more moles of the reagent per mole of methoxy group to be cleaved.

Appropriate solvents for the deprotection reaction are those solvents or mixture of solvents which remain inert throughout the demethylation reaction. Halogenated solvents such as dichloromethane, 1,2-dichloroethane, and chloroform, or aromatic solvents such as benzene or toluene are preferred. The temperature employed in this reaction should be sufficient to effect completion of the demethylation reaction. However, it is advantageous to keep the temperature below 0° C. in order to maximize selectivity for cleavage of the 4'-methoxy group and avoid the formation of undesirable byproducts especially the product 6,4'-dihydroxy analog arising from excessive demethylation. Under the preferred reaction conditions, a selectively dealkylated product will be formed after stirring the reaction for about 1 to 24 hours. A preferred variation involves the use of boron tribromide in the amount of approximately 1.5 moles with one mole of the 6-, 4'-dimethoxy substrate in dichloromethane under a nitrogen atmosphere at a temperature of –20° C. for 1 to 4 hours.

The starting materials for the processes of the present invention may be obtained by a number of routes, including those disclosed in U.S. Pat. No. 4,133,814 and U.S. Pat. No. 4,380,635. The process for preparing compounds of formula I as provided by the instant invention is shown below in Scheme I:

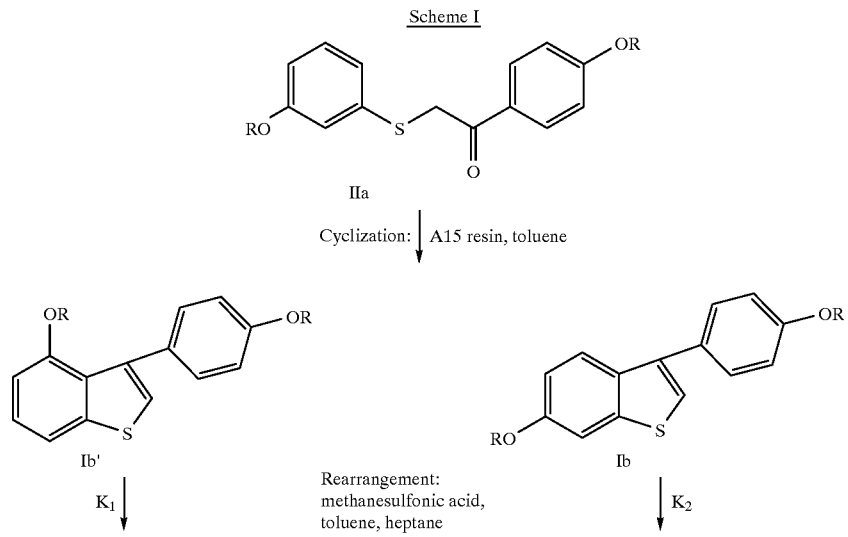

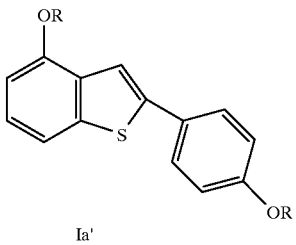

Ia'

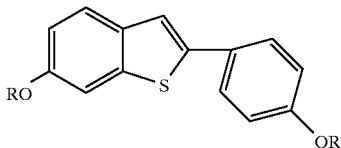

I

The overall reaction process comprises a first cyclization step and a subsequent rearrangement step. A compound of formula I is the desired product. The cyclization reaction in the first step occurs with a variety of acid catalysts, and in general occurs approximately 50–100 times faster than the subsequent rearrangement reaction. The instant invention employs a cation exchange resin as the acid catalyst.

The cyclization reaction rate may be increased by increasing the amount of resin employed in the reaction mixture. The effect of catalyst loading on reaction yields when employing A15 resin as the cation exchange resin was examined. Over the range of 5 to 33 ml catalyst/gram reactant, there was no effect on the yield, or on the level of desmethyl formation. However, the reaction rate is directly proportional to the catalyst loading.

Any cation exchange resin or combination of cation exchange resins may be employed in the cyclization step. Preferred for the practice of the present invention are polystyrene-based cation exchange resins. Particularly preferred are polystyrene-based sulfonic acid catalysts.

The cation exchange resins may be readily separated from the overall reaction mixture by any means including but not limited to filtration, and any recovered resins may be re-used. Filtration may be achieved by any means including the use of Whatman paper, 100 mesh screen, 5–20 micron filter cartridges, and the like.

The reaction is typically run under reflux with the azeotropic removal of water. The effect of water on the activity of sulfonic acid resins in some reactions has been previously discussed by A. R. Pitochelli, *Ion Exchange Catalysis and Matrix Effects*, brochure published by Rohm and Haas, Inc., 1975. See, also, G. Zundel, *Hydration and Intermolecular Interaction Infrared Investigations with Polyelectroyte Membranes*, Academic Press, New York, 1969, and G. Zundel et al., *Physik. Chem.*, 59, 225, 1968.

Various desmethyl side products may form during the reaction. The structures of 4 different desmethyl side products are provided in Scheme II below:

Scheme II

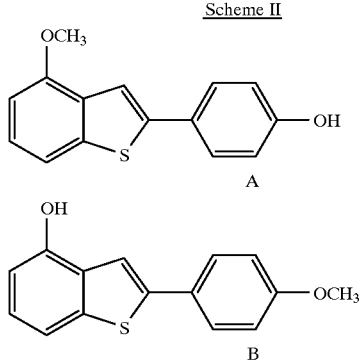

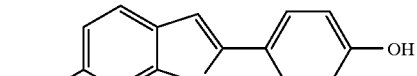

C

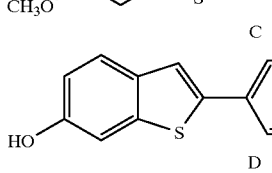

D

Isomers A and B are derived from a compound of formula Ia', while isomers C and D are derived from a compound of formula I. The ratio of isomers A:B:C:D in a typical reaction mixture was roughly 1:1:9:9. Isomer identity was generally confirmed by HPLC. The isomer ratio, and hence the ultimate yield, is determined by the kinetically-controlled cyclization reaction. Using a cation exchange resin in toluene, a preferred isomer ratio of 88:12 (I/Ia') was obtained in the cyclization step, compared to an isomer ratio of 75:25 obtained when using polyphosphoric acid in the cyclization step. Further equilibration between ortho and para isomers during this process was not observed.

The rearrangement reaction is a thermodynamically controlled reaction. The equilibrium constants for said reaction are as follows: $K_1$ is >100, while $K_2$ is approximately 7–9. Using a cation exchange resin and toluene/heptane as the solvent system, a compound of formula Ia precipitates as it forms in the reaction mixture, thereby driving the reaction to completion. The rearrangement of the undesired isomer, a compound of formula Ib', was 3–5 times faster than the rearrangement of the desired isomer, a compound of formula Ib.

Solvents including solvent mixtures and co-solvents employed in the practice of the present invention may affect the overall reaction, including reaction products and overall yield. Typically, the solvent of choice is a very weak base. In addition, the solvent should not solvate the sulfonic acid proton of the resin. The preferred solvent for the practice of the present invention is an aromatic solvent, with reasonable results obtained in both aliphatic and chlorinated solvents. Exemplary solvents include toluene, heptane, xylene, chlorobenzene, dimethoxyethane, and tetrachloroethylene. Preferred for the practice of the present invention is toluene. Particularly preferred is toluene with added methanesulfonic acid. The added methanesulfonic acid facilitates the subsequent rearrangement reaction. Sufficient methanesulfonic acid must be added to the toluene such that a separate MSA phase forms.

Heptane is an additionally preferred solvent, which affects the crystallization of the benzothiophene products. This crystallization produces a dramatic reduction in the solubility of same, hence driving the equilibrium of the reaction. Heptane is best added to the reaction mixture prior to equilbrium.

According to the invention, the cyclization reaction is conducted at temperatures from about 50° C. to about 110° C., preferably from about 75° C. to 110° C., and nd most preferably from about 80 to 110° C. The yield of the cyclization reaction is the same whether the reaction is run at reflux or at 70° C. However, reflux is greatly preferred since the reaction rate is 10–20 times faster. The use of higher temperatures during the reaction is not desirable, as this may lead to increased levels of desmethyl sideproducts.

The acetophenone starting material is heated in the presence of a cation exchange resin and toluene for at least 30 minutes, and preferably from about 60 to 180 minutes. As presently practiced, the acetophenone is cyclized at about 110° C. for about 3–5 hours. Subsequent to this initial heating period, the reaction is cooled to a temperature of from about 50 to 90° C., and the cation exchange resin is removed by filtration. If the reaction is cooled below 50° C., a slight precipitate of benzothiophene may occur, which is a function of the amount of rearrangement which occurred during the cyclization step. Typically, 1–7% rearrangement occurs during the cyclization reaction.

The rearrangement reaction typically occurs in the presence of the methanesulfonic acid and toluene reaction mixture. The further addition of heptane at this time is optional, but may provide enhanced reaction yield. After the addition of heptane during the reaction, an increase in temperature from 90° to 106° is undesirable due to its negative effect on yield.

A suitable solvent or solvent mixture may be further added to the reaction mixture at the end of the rearrangement reaction in order to quench the reaction. An example of a suitable solvent would include but not be limited to isopropanol (IPA), and the like. This solvent addition reduces the solubility of the product, as well as improves the purity of same.

The overall process may be operated as a "one-pot" synthesis, batchwise, semi-continuously, continuously, and the like. One skilled in the art would appreciate the differences between these modes of operation, including which reaction would be employed for a given purpose. For example, in semi-continuous or continuous operation the starting material and solvent are fed to a packed column of the solid acid resin. Recovery and isolation of excess solvent and product may be accomplished by distillation. Further, the reaction is optionally perfomed in the presence of an organic solvent which forms an azeotrope with water, and thus facilitates the removal of by-product by azeotropic distillation during the reaction process. Examples of such solvents which may be employed include aromatic hydrocarbons such as benzene, toluene, xylene, and the like.

The benzothiophene product may be isolated with a standard extractive workup by adding water, separating the layers, optionally extracting the aqueous layer again with the organic solvent, combining the organic layers, and concentrating the combined organic layers. When the starting material is the methoxy derivative, the desired 6-alkoxy compound crystallizes in the concentrated solvent while the 4-alkoxy isomer remains in solution. The desired 6-alkoxy compound may be collected by filtration.

In a preferred cyclization process according to the invention, the starting material is α-(3-methoxyphenylthio)-4-methoxyacetophenone, which yields, upon workup after cyclization, 6-methoxy-2-(4-methoxyphenyl)benzo[b]thiophene. This material may subsequently be converted into a compound of formula III, such as for example, 6-hydroxy-2-(4-hydroxyphenyl)-3-[4-(2-aminoethoxy)benzoyl]benzo[b]thiophene. Conversion of 6-alkoxy-2-(4-alkoxyphenyl)benzo[b]thiophene to compounds of formula III may be accomplished according to the reactions as provided in U.S. Pat. No. 4,380,635.

The compounds of formula III are very often administered in the form of acid addition salts. The salts are conveniently formed, as is usual in organic chemistry, by reacting the compound prepared according to this invention with a suitable acid. The salts are quickly formed in high yields at moderate temperatures, and often are prepared by merely isolating the compound from a suitable acidic wash as the final step of the synthesis. For example, salts may be formed with inorganic or organic acids.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The following group of compounds are provided as a further illustration of the overall process disclosed herein:

6-hydroxy-2-(4-hydroxyphenyl)-3-[4-(2-dimethylaminoethoxy)-benzoyl]benzo[b]thiophene;

3-[4-(2-ethoxymethylaminoethoxy)benzoyl]-6-hydroxy-2-(4-hydroxylphenyl)benzo[b]thiophene;

3-[4-(2-ethoxylisopropylaminoethoxy)benzoyl]-6-hydroxy-2-(4-hydroxyphenyl))benzo[b]thiophene;

3-(4-(2-dibutylaminoethoxy)benzoyl]-5-hydroxy-2-(4-hydroxyphenyl)benzo[b]thiophene;

3-[4-(2-(1-methylpropyl)methylaminoethoxy]-benzoyl]-6-hydroxy-2-(4-hydroxyphenyl)benzo[b]thiophene;

6-hydroxy-2-(4-hydroxyphenyl)-3-[4-[2-di(2-methylpropyl)aminoethoxy]benzoyl]benzo[b]thiophene;

6-hydroxy-2-(4-hydroxyphenyl)-3-[4-(2-pyrrolidinoethoxy)benzoyl]benzo[b]thiophene;

6-hydroxy-2-(4-hydroxyphenyl)-3-[4-(2-piperidinoethoxy)benzoyl]benzo[b]thiophene;

6-hydroxy-2-(4-hydroxyphenyl)-3-[4-(2-morpholinoethoxy)-benzoyl]benzo[b]thiophene;

3-[4-(2-hexamethyleneiminoethoxy)benzoyl]-6-hydroxy-2-(4-hydroxyphenyl)benzo[b]thiophene.

The following Examples are provided to better elucidate the practice of the present invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

EXAMPLES

All experiments were run under positive pressure of dry nitrogen. All solvents and reagents were used as obtained. The percentages are generally calculated on a weight (w/w) basis; except for high performance liquid chromatography (HPLC) solvents which are calculated on a volume (v/v) basis. Proton nuclear magnetic resonance ($^1$H NMR) spectra and $^{13}$C nuclear magnetic resonance spectra ($^{13}$C NMR) were obtained on a Bruker AC-300 FTNMR spectrometer at 300.135 MHz or a GE QE-300 spectrometer at 300.15 MHz. Silica-gel flash chromatography may be performed as described by Still et al. using Silica Gel 60 (230–400 mesh, E. Merck). Still et al., *J. Org. Chem.*, 43, 2923 (1978). Elemental analyses for carbon, hydrogen, and nitrogen were determined on a Control Equipment Corporation 440 Elemental Analyzer. Elemental analyses for sulfur were determined on a Brinkman Colorimetric Elemental Analyzer. Melting points were determined in open glass capillaries on a Gallenkamp hot air bath melting point apparatus or a Mettler FP62 Automatic instrument, and are uncorrected. Field desorption mass spectra (FDMS) were obtained using a Varian Instruments VG 70-SE or VG ZAB-3F mass spectrometer. High resolution free atom bombardment mass spectra (FABMS) were obtained using a Varian Instruments VG ZAB-2SE mass spectrometer.

The yields of 6-methoxy-2-(4-methoxyphenyl) benzo[b] thiophene may be determined by high performance liquid chromatography (HPLC) in comparison to an authentic sample of this compound prepared by published synthetic routes. See, for example, U.S. Pat. No. 4,133,814.

Example 1

Cyclization 40 g α-(3-methoxyphenylthio)-4-methoxyacetophenone, 4 g dry Amberlyst® 15 (A15) resin (available from Rohm & Haas), and 120 ml Toluol (Drum Stock) was added to a 1 liter, 3 neck round bottom flask, equipped with a reflux condenser and a Dean Stark trap. The trap is either prefilled with toluene, or extra solvent is added to the reactor. The mixture was heated to reflux and stirred for 3–5 hours while azeotropically removing the water. This mixture was then cooled to 50–70° C. The resin was filtered off using a 4.25 cm Buchner funnel, and washed with 20 ml toluene. The total weight of the filtrate was recorded, and the volume of toluene needed to use as a rinse for transfer of the filtrate to a 500 ml rearrangement flask was calculated. [rinse volume= (WT.–161.5)/0.866.][Note: this volume of rinse accounts for evaporation loss which occurs during hot toluene filtration.]

Rearrangement

The filtrate was transferred to a 500 ml roundbottom flask equipped with a reflux condenser. 14 g methanesulfonic acid (MSA) was added over 2–5 minutes with a dropping funnel. The mixture was rinsed with 3 ml toluene, and stirred at 90° C. for 3–5 hours. 56 mls of heptane (Drum Stock) was added over 5–20 minutes. The mixture was then stirred at 90° C. for 1 hour, and stirred at 80° C. for 3–4 hours 98 mls of isopropanol (IPA) (Drum Stock) was added over 5–20 minutes, and then refluxed for 30 minutes at approximately 83° C. The mixture was then cooled to 0° C. at a rate no faster than 50° C. per hour. This was then stirred for at least 1 hour at 0° C., filtered, washed twice with 75 ml 70/30 (Toluol/IPA), and dried at 60° C. under full vacuum. Yield= 77–80.4%; 1000% potency; 0.1% desmethyl; 0.1% Compound D; 0.3% TRS.

Example 2

The following reaction was performed in the pilot plant. The cyclization and rearrangement were both conducted in 50 gallon Hastelloy C reactors. Unless otherwise noted, the reaction conditions are as indicated in Example 1.

Cyclization

α-(3-methoxyphenylthio)-4-methoxyacetophenone: 14 kg
A15 resin: 1.4 kg
Toluene: 42 liters
Cyclization reflux time: 2.5 hours
A15 toluene rinse: 6 liters
A15 resin filtration temperature: 60° C.

Rearrangement

MSA: 4.9 kg
MSA/toluene rinse: 1 liter
Stir time at 90° C. before heptane: 3 hr
Stir time at 90° C. after heptane: 1 hr
Stir time at 80° C. after heptane: 3 hr
Heptane: 20 liters
Heptane addition time: 20 minutes
IPA quench amount: 34 liters
IPA addition time: 17 minutes
Reflux time after IPA addition: 30 minutes
Cooling rate: 50° C. per hour
Final temp before product filtration: 0° C.
Cake wash: 2×26 liters of 70/30 toluene/IPA
The results obtained were:
77.5% yield
100.1% potency
0.210% rel subs
0.08% desmethyl

Example 3

The reaction conditions used for this were identical to those in Example 2 except for the following variables: 50 gallon glass-lined reactors were used in place of the 50 gallon Hastelloy reactors; the stir time at 90° C. before heptane addition was increased to 4 hours; and the stir time at 80° C. after heptane addition was increased to 4 hours. The results obtained were as follows:

55% yield
99.5% potency
0.30% rel subs
0.09% desmethyl

Example 4

The following reaction was performed in the pilot plant: The cyclization and rearrangement were both conducted in a 50 gallon glass-lined reactor. Unless otherwise noted, the reaction conditions are as indicated in Example 1. The amount of α-(3-methoxyphenylthio)-4-methoxyacetophenone was increased to 16.5 kg, and all other charges were scaled accordingly. The total volume in the reaction vessel was therefore increased. The agitation of the reaction mixture was increased from 95 to 115 rpm. The results obtained were:

79.6% yield
100.60% potency
0.25% rel subs
0.08% desmethyl

I claim:
1. A process for preparing a compound of formula Ib

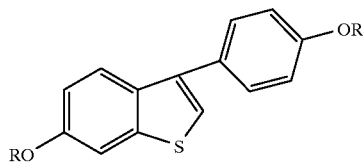

wherein the R groups are the same or different and represent $C_1$–$C_6$ alkyl,
which comprises:
cyclizing a dialkoxy compound of formula II

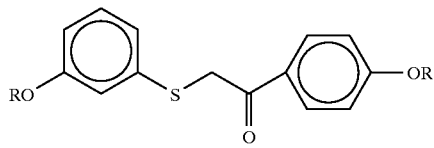

in the presence of a cation exchange resin.

2. A process according to claim 1 which further comprises preparing a compound of formula I

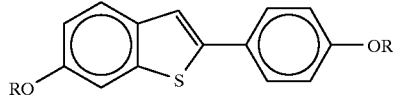

wherein the R groups are the same or different and represent $C_1$–$C_6$ alkyl; by rearranging a compound of formula Ib.

3. A process according to claim 1, wherein R is methyl.
4. A process according to claim 1, wherein said cation exchange resin is a polystyrene-based sulfonic acid resin.
5. A process according to claim 1, which further comprises contacting the reaction mixture with methanesulfonic acid in toluene.
6. A process according to claim 5, which further comprises contacting said reaction mixture with heptane.

7. A process according to claim 6, which further comprises contacting said reaction mixture with isopropanol.
8. A process according to claim 1, wherein said cyclization is carried out at a temperature of from about 70° C. to about 90° C.
9. A process according to claim 1, wherein said process is carried out as a batch operation.
10. A process according to claim 1, wherein said process is carried out as a continuous operation.
11. In a process for preparing a compound of formula III

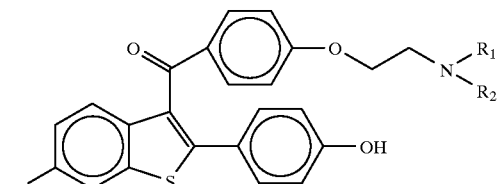

wherein:
$R_1$ and $R_2$ are independently $C_1$–$C_6$ alkyl, or combine to form, with the nitrogen to which they are attached, piperidinyl, pyrrolidinyl, methylpyrrolidinyl, dimethylpyrrolidinyl, or hexamethyleneimino, or the pharmaceutically acceptable salts or solvates thereof;
the improvement which comprises:
cyclizing a compound of formula II

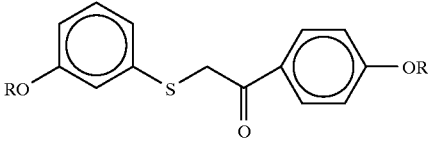

wherein the R groups are the same or different, and represent $C_1$–$C_6$ alkyl, in the presence of a cation exchange resin.

12. A process according to claim 11, wherein R is methyl.

* * * * *